(12) United States Patent
Wiegert et al.

(10) Patent No.: US 8,290,116 B2
(45) Date of Patent: Oct. 16, 2012

(54) IMAGING APPARATUS INCLUDING CORRECTION UNIT FOR SCATTERED RADIATION

(75) Inventors: Jens Wiegert, Aachen (DE); Matthias Bertram, Aachen (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 13/063,486

(22) PCT Filed: Sep. 9, 2009

(86) PCT No.: PCT/IB2009/053936
§ 371 (c)(1),
(2), (4) Date: Mar. 11, 2011

(87) PCT Pub. No.: WO2010/032163
PCT Pub. Date: Mar. 25, 2010

(65) Prior Publication Data
US 2011/0164722 A1   Jul. 7, 2011

(30) Foreign Application Priority Data
Sep. 16, 2008 (EP) .................................... 08164401

(51) Int. Cl.
*A61B 6/00* (2006.01)
*G01D 18/00* (2006.01)
(52) U.S. Cl. .............................. 378/7; 378/147; 378/207
(58) Field of Classification Search ........................ 378/7
See application file for complete search history.

(56) References Cited

U.S. PATENT DOCUMENTS

| | | | |
|---|---|---|---|
| 4,809,172 A | 2/1989 | Hopkinson et al. | |
| 5,394,454 A * | 2/1995 | Harding | 378/86 |
| 6,618,466 B1 | 9/2003 | Ning | |
| 6,823,043 B2 * | 11/2004 | Fewster et al. | 378/86 |
| 7,065,234 B2 | 6/2006 | Du et al. | |
| 7,190,758 B2 * | 3/2007 | Hagiwara | 378/7 |
| 7,283,613 B2 * | 10/2007 | Harding | 378/86 |
| 7,477,725 B2 * | 1/2009 | Harding | 378/57 |
| 7,535,987 B2 * | 5/2009 | Matsuda | 378/7 |
| 2007/0165772 A1 * | 7/2007 | Sainath et al. | 378/7 |

(Continued)

FOREIGN PATENT DOCUMENTS

JP   61083983 A  *  4/1986

(Continued)

OTHER PUBLICATIONS

Bertram et al., Scatter correction for cone-beam computed tomography using simulated object models, Medical Imaging, Proc. of SPIE, vol. 6142, 2006, pp. 1-12.*

(Continued)

*Primary Examiner* — Alexander H Taningco

(57) ABSTRACT

The present invention relates to an imaging apparatus for generating an image of a region of interest of an object. The imaging apparatus comprises a radiation source (2) for emitting radiation (4) and a detector (6) for measuring the radiation (4) after having traversed the region of interest and for generating measured detection values depending on the measured radiation (4). The imaging apparatus further comprises an attenuation element for attenuating the radiation (4) before traversing the region of interest and an attenuation element scatter values providing unit (12) for providing attenuation element scatter values, which depend on scattering of the radiation (4) caused by the attenuation element. A detection values correction unit (17) corrects the measured detection values based on the provided attenuation element scatter values, and a reconstruction unit (18) reconstructs an image of the region of interest from the corrected detection values.

16 Claims, 8 Drawing Sheets

U.S. PATENT DOCUMENTS

2007/0268997 A1* 11/2007 Zhu et al. .................... 378/7

FOREIGN PATENT DOCUMENTS

| JP | 06014911 A * | 1/1994 |
| --- | --- | --- |
| WO | 2006070316 A1 | 7/2006 |
| WO | 2007148263 A1 | 12/2007 |

OTHER PUBLICATIONS

Wiegert et al., Model Based Scatter Correction for Cone-Beam Computed Tomography, Medical Imaging, Proc. of SPIE, vol. 5745, 2005, pp. 271-282.*

Ay et al: "Development and Validation of MCNP4C-Based Monte Carlo Simulator for Fan-And-Cone-Beam X-Ray CT"; Physics in Medicine and Biology, 2005, vol. 50, No. 20, pp. 4863-4885.

Watson, C.: "New, Faster, Image-Based Scatter Correction for 3D PET"; IEEE Transactions on Nuclear Science, Aug. 2000, vol. 47, No. 4, pp. 1587-1594.

Bertram et al: "Potential of Software-Based Scatter Corrections in Cone-Beam Volume CT"; Medical Imaging 2005: Physics of Medical Imaging, Proceedings of SPIE, vol. 5745, pp. 259-270.

Zbijewski et al: "Efficient Monte Carlo Based Scatter Artifact Reduction in Cone-Beam Micro-CT"; IEEE Transactions on Medical Imaging, Jul. 2006, vol. 25, No. 7, pp. 817-827.

Zaidi et al: "Current Status and New Horizons in Monte Carlo Simulation of X-Ray CT Scanners"; Medical and Biological Engineering and Computing, 2007, vol. 45, No. 9, pp. 809-817.

\* cited by examiner

IMAGING APPARATUS INCLUDING CORRECTION UNIT FOR SCATTERED RADIATION

FIELD OF THE INVENTION

The invention relates to an imaging apparatus, an imaging method and an imaging computer program for generating an image of a region of interest of an object. The invention relates further to a correction apparatus, a correction method and a correction computer program for correcting detection values acquired by an imaging apparatus.

BACKGROUND OF THE INVENTION

U.S. Pat. No. 7,065,234 B2 discloses a computed tomography system comprising a radiation source emitting radiation and a detector for detecting the radiation after having traversed a region of interest for generating detection values depending on the detected radiation. The detection values are corrected with respect to scatter effects and the corrected detection values are used for reconstructing an image of the region of interest. This reconstructed image still comprises image artifacts, which are caused by scatter effects, thereby reducing the quality of the reconstructed image.

SUMMARY OF THE INVENTION

It is an object of the present invention to provide an imaging apparatus, an imaging method and an imaging computer program for generating an image of a region of interest of an object, wherein the quality of a reconstructed image of the region of interest is improved. It is a further object of the present invention to provide a correction apparatus, a correction method and a correction computer program for correcting detection values, which correct the detection values such that the quality of an image, which is reconstructed by using the corrected detection values, is improved.

In a first aspect of the present invention an imaging apparatus for generating an image of a region of interest of an object is presented, wherein the imaging apparatus comprises:

a radiation source for emitting radiation, a detector for measuring the radiation after having traversed the region of interest and for generating measured detection values depending on the measured radiation, an attenuation element for attenuating the radiation before traversing the region of interest, an attenuation element scatter values providing unit for providing attenuation element scatter values, which depend on scattering of the radiation caused by the attenuation element, a detection values correction unit for correcting the measured detection values based on the provided attenuation element scatter values, a reconstruction unit for reconstructing an image of the region of interest from the corrected detection values.

The detection values, which are measured by the detector, are adversely affected by the scattering of the radiation in the attenuation element. Thus, by correcting the detection values with respect to the scattering of the radiation in the attenuation element, i.e. by providing attenuation element scatter values, which depend on scattering of the radiation caused by the attenuation element and by correcting the detection values based on the determined attenuation element scatter values, the quality of the detection values and, thus, of the image, which is reconstructed from the corrected detection values, is improved.

The imaging apparatus is preferentially a computed tomography apparatus, wherein an X-ray source emits X-ray radiation and is rotated with respect to the region of interest of the object for illuminating the region of interest from different angular directions. The detector detects the radiation, which has been used for illuminating the region of interest from different directions, after having traversed the attenuation element and the region of interest and generates detection values, which depend on the detected radiation. The attenuation element of the computed tomography apparatus is preferentially a wedge. The wedge can also be called bow tie or beam shaper. The wedge is used in the computed tomography apparatus in order to lower the amount of radiation that goes through the object, which is preferentially a patient, in lateral object areas. In particular, the wedge is thick where the kind of object, which is supposed to be imaged, in particular, a patient, is thin and the wedge is thin where the kind of object, which is supposed to be imaged, is expected to be thick. The attenuation element scatter values providing unit provides attenuation element scatter values, which depend on the scattering of the X-ray radiation in the wedge, and the detection values correction unit corrects the measured detection values based on the determined attenuation element scatter values. The reconstruction unit is preferentially adapted to reconstruct an image of the region of interest from the corrected detection values using a backprojection algorithm or another computed tomography reconstruction algorithm.

The term "region of interest" includes the entire object or only a part of the object.

The radiation forms preferentially a beam like a cone beam or a fan beam, wherein the object is preferentially sized and arranged such that the object is completely located within the beam in a direction perpendicular to a rotational axis, if the radiation source is adapted to rotate around the rotational axis while measuring the detection values.

It should be noted that the term "correcting the measured detection values based on the provided attenuation element scatter values" also includes that the attenuation element scatter values are further processed, for example, in order to consider the attenuation of the object, wherein the measured detection values are preferentially corrected based on these further processed attenuation element scatter values, It is preferred that the imaging apparatus further comprises an object scatter determination unit for determining object scatter values, which depend on the scattering of the radiation by the object, wherein the detection values correction unit is adapted to correct the measured detection values based on the determined object scatter values. Since the detection values can also be adversely affected by scattering of the radiation in the object, the consideration of these additional scattering effects, i.e. the determination of object scatter values, which depend on the scattering of the radiation in the object, and the correction of the detection values also based on the determined object scatter values, further increases the quality of the detection values and, thus, of the image of the region of interest, which is reconstructed by using the corrected detection values.

The determination of the object scatter values and the correction of the measured detection values based on the determined object scatter values is preferentially performed by known methods, in particular, by a separate method based on convolution with object specific convolution kernels as disclosed in, for example, WO 2007/148263 A1, which is herewith incorporated by reference.

It is further preferred that the imaging apparatus comprises an examination zone, in which the object is to be located, and a collimator for collimating the radiation emitted by the radiation source, the collimator being located between the attenuation element and the examination zone, wherein the radiation source, the detector and the collimator are adapted to measure calibration values for different collimations of the radiation and wherein the attenuation element scatter values providing unit is adapted to determine the attenuation element scatter values based on the calibration values. Preferentially, the attenuation element scatter values providing unit is adapted to determine the attenuation element scatter values by fitting a function, which considers an attenuation element scatter part and an unscattered part of the calibration values and which depends on the different collimations, to the calibration values. It is further preferred that the function has a square-root dependence for describing the increasing attenuation element scatter part of the calibration values with increasing collimation and a constant dependence for describing the unscattered part of the calibration values, wherein the attenuation element scatter values depend on the attenuation element scatter part. Since the part of the detection values, which is caused by the scattering of the radiation in the attenuation element, has a square-root behavior depending on the collimation of the radiation, this part and, thus, the attenuation element scatter values, which depend on this part, can easily and with high accuracy be determined by fitting a function having a square-root dependence to the calibration values, which have been measured for different collimations of the radiation.

It is further preferred that the detector comprises several detector elements, the radiation source, the detector and the collimator are adapted to measure calibration values for different collimations of the radiation for a sub-group of the detector elements, the attenuation element scatter values providing unit is adapted to determine the attenuation element scatter values for the sub-group of the detector elements, the imaging apparatus further comprises an attenuation element scatter value ratio providing unit for providing ratios of the attenuation element scatter values of the sub-group of detector elements to attenuation element scatter values of detector elements outside of the sub-group, the attenuation element scatter values providing unit is adapted to determine attenuation element scatter values for detector elements outside of the sub-group by multiplying the attenuation element scatter values for the sub-group by the provided ratios. This allows measuring the calibration values and determining the attenuation element scatter values based on the calibration values only for the sub-group of detector elements and determining the attenuation element scatter values for the other detector elements just by multiplying the attenuation element scatter values of the sub-group of detector elements by the provided ratios, thereby reducing the effort and the time needed for determining the attenuation element scatter values.

It is further preferred that the detector comprises a two-dimensional detection surface, wherein the sub-group of detector elements is a line of detector elements on the detection surface. The line is preferably a central line, in particular, the line is preferably centered with respect to a direction, which is parallel to the rotational axis if the imaging apparatus is a computed tomography apparatus.

The radiation source, the collimator and the detector are preferentially adapted such that for each collimation, which is used for determining the calibration values, the sub-group of detector elements, preferentially the line of detector elements, further preferred the central line of the detector elements, is completely illuminated.

The attenuation element scatter value ratio providing unit is preferentially a simulation unit, wherein the generation of the attenuation element scatter values is modeled by modeling the imaging apparatus, in particular, by modeling the radiation source, the detector and the attenuation element, and by performing a Monte-Carlo simulation. If the imaging apparatus is a computed tomography apparatus, the attenuation element scatter value ratio providing unit is preferentially adapted to provide for each combination of the central line of detector elements, which is perpendicular to the rotational axis, with another line of detector elements, which is also perpendicular to the rotational axis, a ratio of attenuation element scatter values, in particular, a single ratio of attenuation element scatter values.

In an embodiment, the attenuation element scatter value ratio providing unit is a storing unit, in which the attenuation element scatter value ratios are stored already, or it can calculate these ratios, for example, by using the above described simulation, wherein preferentially for each pair of detector elements, which are located on a same line parallel to the rotational axis and which are located on the central line of detector elements, which is perpendicular to the rotational axis, and another, further line of detector elements, which is also perpendicular to the rotational axis, an attenuation element scatter value ratio is determined and wherein the attenuation element scatter value ratios, which have been determined for the central line and a single further line, are averaged for determining a single attenuation element scatter value ratio for the combination of the central line, which is perpendicular to the rotational axis, and the single further line, which is also perpendicular to the rotational axis. This reduces the amount of attenuation element scatter value ratios, which have to be provided by the attenuation element scatter value ratio providing unit.

It is further preferred that the imaging apparatus further comprises:

an air scan values providing unit for providing air scan values and an air scan values correction unit for correcting the air scan values based on the attenuation element scatter values, wherein the detection values correction unit is adapted to correct the detection values based on the corrected air scan values.

The imaging apparatus is, for example, a computed tomography apparatus and illuminates the region of interest from different directions, wherein the different directions are preferentially divided in different angular ranges of, for example, 10 degrees. The air scan values are preferentially determined by acquiring detection values, while an object is not present in the region of interest and the radiation source rotates around the region of interest, and by averaging detection values, which belong to the same angular range for determining an air scan value for the respective angular range. Thus, preferentially for different acquisition conditions an air scan value is determined for each angular range. An acquisition condition is defined by, for example, the tube current of the radiation source if the radiation source is an X-ray tube, the collimation, the rotational speed et cetera. Since the detection values correction unit uses air scan values, which have been corrected based on the attenuation element scatter values, for correcting the detection values, the quality of the detection values and, thus, of the image, which is reconstructed by using the corrected detection values, is further improved. The air scan values providing unit is preferentially a storing unit, in which the air scan values are stored already. In another embodiment, the air scan values providing unit determines the air scan values, for example, by averaging detection values, which have been acquired while an object is not present in the region of interest, as described above.

It is further preferred that the detection values correction unit is adapted to adapt the attenuation element scatter values to the attenuation of radiation, which has been scattered in the attenuation element and attenuated by the object if the object is present between the attenuation element and the detector, and to correct the measured detection values based on the adapted attenuation element scatter values. This adaptation is preferentially performed based on the measured detection values. Since in a measurement for measuring detection values of an object the radiation, which has been scattered by the attenuation element, is attenuated by the object, the attenuation element scatter values, which consider the scattering of the radiation caused by the attenuation element without considering an attenuation of the scattered radiation by the object, have to be adapted such that this attenuation by the object is considered. This could also be defined as a propagation of the attenuation element scatter values through the object. This adaptation of the attenuation element scatter values to the attenuation of the object or the propagation of the attenuation element scatter values through the object, respectively, further improve the quality of the corrected detection values and, thus, of an image reconstructed by using the corrected detection values.

It is further preferred that the adaptation of the attenuation element scatter values is performed by multiplying the respective attenuation element scatter value by a respective object attenuation value that depends on the attenuation caused by the object. The object attenuation value is preferentially the respective attenuation caused by the object or a low-pass filtered value of this attenuation caused by the object. This low-pass filter comprises preferentially low-pass filter coefficients, which are adapted as a function of the system geometry and an acceptance angle of a used anti-scatter grid, which is located between detector elements of the detector. These low-pass filter coefficients are adapted such that the filtered attenuation caused by the object, i.e. the object attenuation value in this case, reflects the average attenuation caused by the object, seen from the detector pixel and integrated over the entire acceptance angle of the anti-scatter grid. Therefore, it is further preferred that the low pass filter is two-dimensional and that the low-pass coefficients are chosen individually for each detector dimension. In one preferred embodiment the low-pass filter is implemented as a binomial low-pass filter.

It is further preferred that
the imaging apparatus comprises:
a) an air scan values providing unit for providing air scan values and
b) an air scan values correction unit for correcting the air scan values based on the attenuation element scatter values,
the detection values correction unit is adapted to correct the measured detection values iteratively, wherein
a) in an iteration step the corrected detection value is calculated by subtracting the respective attenuation element scatter value multiplied by a respective object attenuation value, that depends on the attenuation caused by the object (31), from the respective measured detection value divided by the respective corrected air scan value,
b) initially the respective object attenuation value depends on the respective measured detection value divided by the respective corrected air scan value, and in further iteration steps the object attenuation value depends on a calculated respective corrected detection value, i.e. the calculated respective detection value that has been calculated in the previous iteration step.

It is further preferred that the detection values correction apparatus is further adapted to also subtract the respective object scatter value divided by the respective corrected air scan value from the respective measured detection value divided by the respective corrected air scan value for calculating the corrected detection value, in particular, in the iteration step.

It should be understood that the attenuation element scatter values, the object scatter values, the corrected air scan values and the object attenuation values are assigned to the respective detection values. For example, an attenuated attenuation element scatter value, an object scatter value, a corrected air scan value and an object attenuation value are assigned to a detection value, which corresponds to the same detector element of the detector and to the same acquisition condition, i.e., for example, to the same angular position of the radiation source, the same collimation, the same tube current if the radiation source is an X-ray tube et cetera. A respective attenuation element scatter value, a respective object scatter value, a respective corrected air scan value and a respective object attenuation value are preferentially assigned to the same detection value.

The imaging apparatus is preferentially adapted to determine for each combination of detector element of the detector and acquisition condition an attenuation element scatter value. It is further preferred that the imaging apparatus determines for each of these combinations an object scatter value, an object attenuation value and a corrected air scan value.

In an embodiment, the attenuation element scatter values providing unit is a storing unit, in which the attenuation element scatter values are stored already. The attenuation element scatter values providing unit can also be adapted to determine the attenuation element scatter values by simulations, for example, by a Monte-Carlo simulation, of the imaging apparatus.

In a further aspect of the present invention a correction apparatus for correcting measured detection values is presented, the correction apparatus being provided with the measured detection values generated depending on measured radiation, which has been emitted by a radiation source and which has traversed an attenuation element for attenuating the radiation before traversing a region of interest, the correction apparatus comprising:
an attenuation element scatter values providing unit for providing attenuation element scatter values, which depend on scattering of the radiation caused by the attenuation element,
a detection values correction unit for correcting the measured detection values based on the provided attenuation element scatter values.

It is preferred that the correction apparatus further comprises a reconstruction unit for reconstructing an image of the region of interest from the corrected detection values.

In a further aspect of the present invention, an imaging method for generating an image of a region of interest of an object is presented, wherein the imaging method comprises following steps:
emitting radiation by a radiation source,
attenuating the radiation before traversing the region of interest by an attenuation element,
measuring the radiation after having traversed the region of interest and generating measured detection values depending on the measured radiation by a detector, providing attenuation element scatter values, which depend on the scattering of the radiation caused by the attenuation element, by an attenuation element scatter values providing unit, correcting the measured detection values based on the provided attenuation element scatter values by a detection values correction unit, reconstructing an image of the region of interest from the corrected detection values by a reconstruction unit.

In a further aspect of the present invention a correction method for correcting measured detection values is presented, wherein the correction method comprises following steps:

providing the measured detection values generated depending on measured radiation, which has been emitted by a radiation source and which has traversed an attenuation element for attenuating the radiation before traversing a region of interest, providing attenuation element scatter values, which depend on scattering of the radiation caused by the attenuation element, by an attenuation element scatter values providing unit, correcting the measured detection values based on the provided attenuation element scatter values by a detection values correction unit.

It is preferred that the correction method further comprises the step of reconstructing an image of the region of interest from the corrected detection values by a reconstruction unit.

In a further aspect of the present invention an imaging computer program for generating an image of a region of interest of an object is presented, wherein the imaging computer program comprises program code means for causing an imaging apparatus as defined in claim 1 to carry out the steps of the imaging method as defined in claim 12, when the imaging computer program is run on a computer controlling the imaging apparatus.

In a further aspect of the present invention a correction computer program for correcting detection values is presented, wherein the correction computer program comprises program code means for causing a correction apparatus as defined in claim 11 to carry out the steps of the correction method as defined in claim 13, when the correction computer program is run on a computer controlling the correction apparatus.

It shall be understood that the imaging apparatus of claim 1, the correction apparatus of claim 11, the imaging method of claim 12, the correction method of claim 13, the imaging computer program of claim 14 and the correction computer program of claim 15 have similar and/or identical preferred embodiments as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
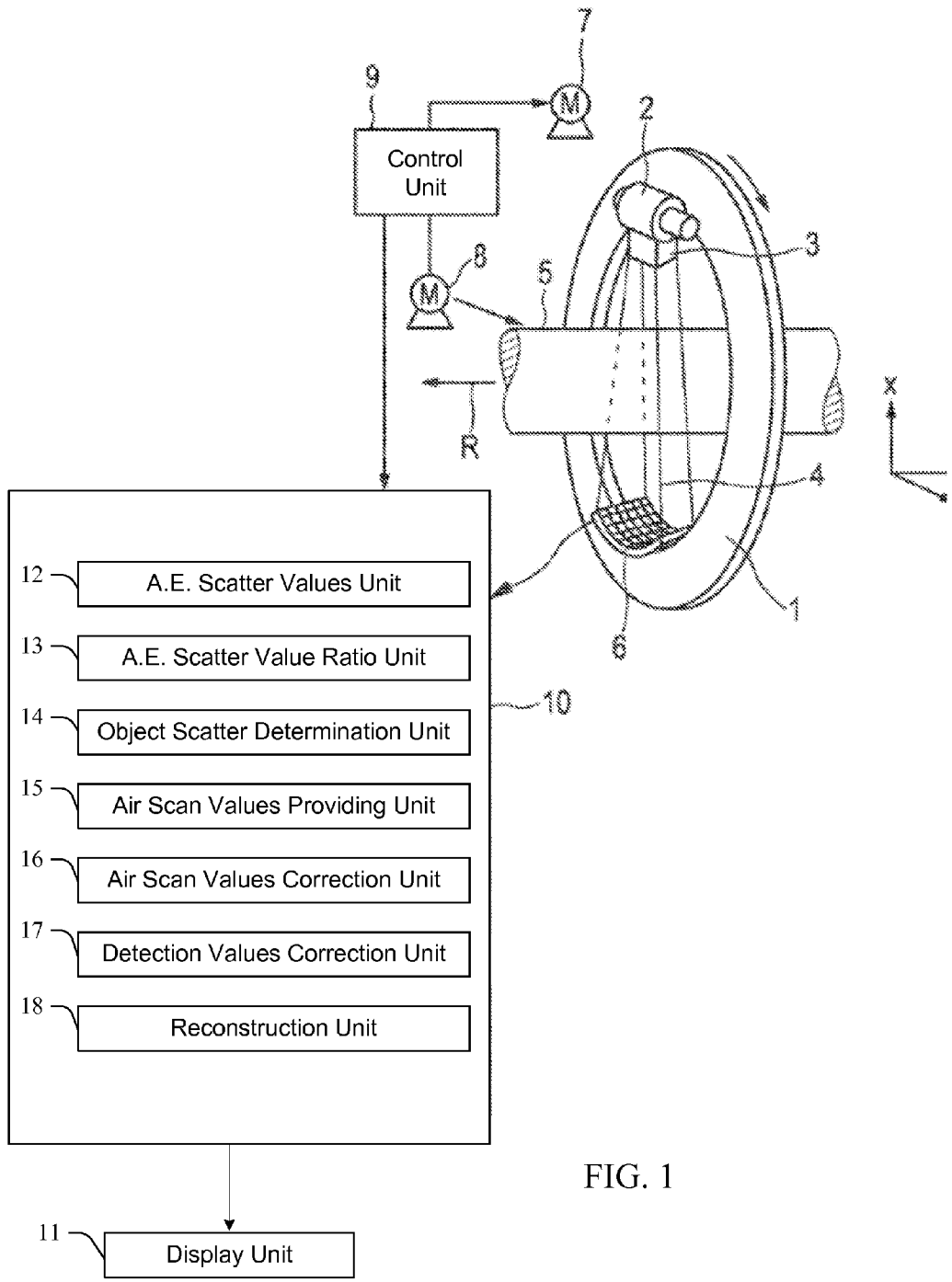
FIG. 1 shows schematically and exemplarily an embodiment of an imaging apparatus for generating an image of a region of interest of an object.

FIG. 1 shows schematically and exemplarily an imaging apparatus for imaging a region of interest of an object. In this embodiment, the imaging apparatus is a computed tomography apparatus. The computed tomography apparatus includes a gantry 1, which is capable of rotation around a rotational axis R, which extends parallel to the z direction. A radiation source 2, which is, in this embodiment, an X-ray tube, is mounted on the gantry 1. The radiation source 2 is provided with a collimator 3, which forms, in this embodiment, a conical radiation beam 4 from the radiation generated by the radiation source 2. The radiation traverses an object (not shown in FIG. 1), such as a patient, and a region of interest, which is preferentially located within the object, in an examination zone 5, which is, in this embodiment, cylindrical. After having traversed the examination zone 5 the radiation 4 is incident on a detector 6, which comprises a two-dimensional detection surface. The detector 6 is mounted on the gantry 1.

The computed tomography apparatus comprises two motors 7, 8. The gantry is driven at a preferably constant but adjustable angular speed by the motor 7. The motor 8 is provided for displacing the object, for example, the patient, who is arranged on a patient table in the examination zone 5, parallel to the direction of the rotational axis R or the z axis. These motors 7, 8 are controlled by a control unit 9, for instance, such that the radiation source 2 and the examination zone 5 and, thus, the region of interest within the examination zone 5, move relative to each other along a helical trajectory. However, it is also possible that the object or the examination zone 5 is not moved, but that only the radiation source 2 is rotated, i.e. that the radiation source 2 moves along a circular trajectory relative to the object or the examination zone 5. Furthermore, in another embodiment, the collimator 3 can be adapted to form another beam shape, in particular, a fan beam, and the detector 6 can comprise a detection surface, which is shaped according to the other beam shape, in particular, to the fan beam.

During a relative movement of the radiation source 2 and the examination zone 5, the detection device 6 generates detection values depending on the radiation incident on the detection surface of the detector 6.

Figure 2:
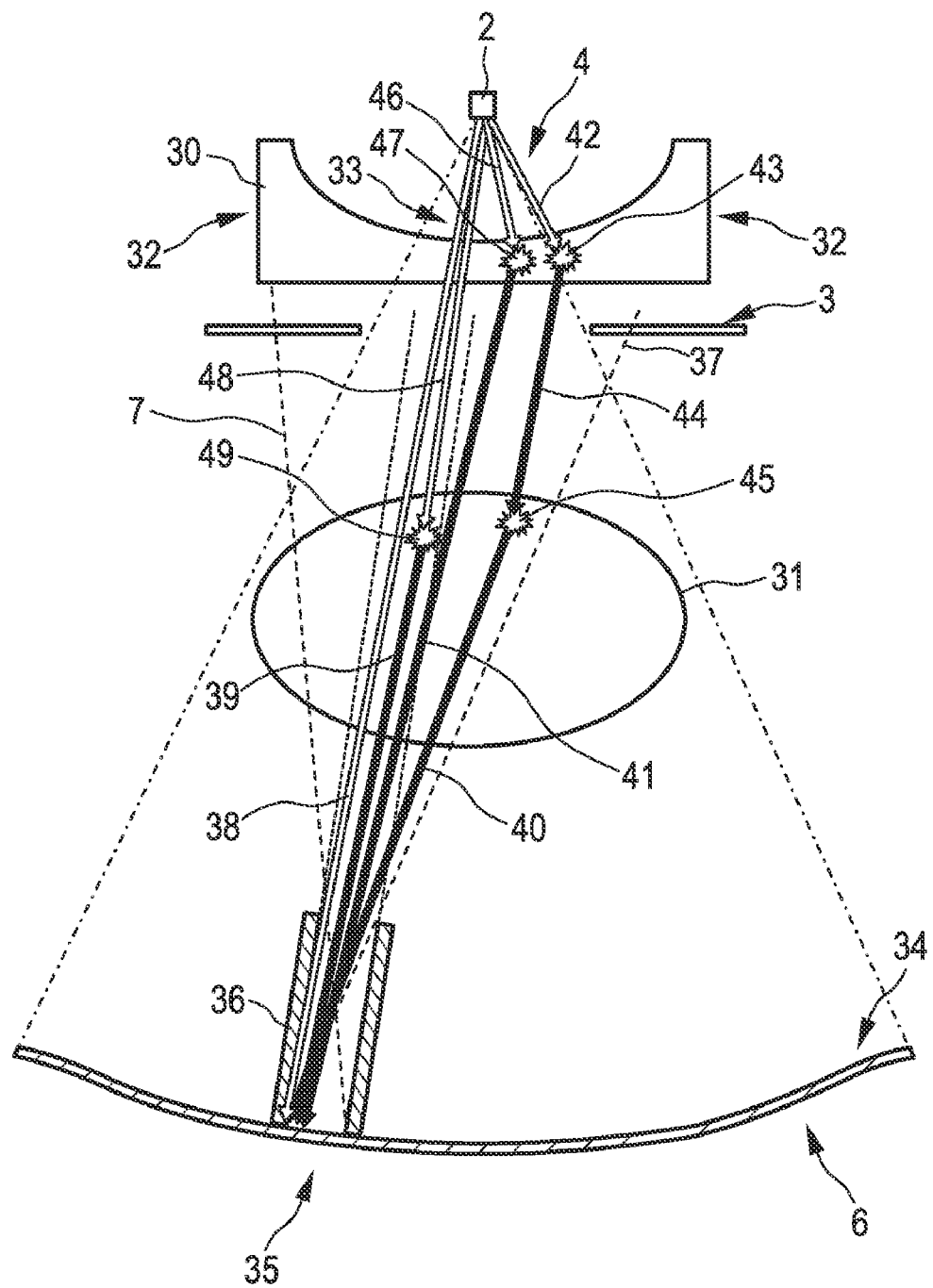
FIG. 2 shows schematically and exemplarily an arrangement of several elements of the imaging apparatus.

The imaging apparatus, i.e. the computed tomography apparatus in this embodiment, further comprises an attenuation element 30 for attenuating the radiation 4 before traversing the object 31 and, thus, the region of interest. The attenuation element 30 is exemplarily and schematically shown in FIG. 2. The attenuation element 30 shown in FIG. 2 is a wedge shaped such that it has a larger thickness in a region 32, through which beams of the radiation 4 traverse, which traverse only a thinner part of the object, which is supposed to be a patient, and a thinner region 33, which is located along radiation beams, which traverse through a thicker region of the object 31. The attenuation element 30 is preferentially shaped like a cuboid having a centered depression, which is elliptically shaped in an intersection plane, which is perpendicular to the rotational axis R or the z direction.

With reference to FIG. 2, the detector 6 comprises a two-dimensional detection surface 34 comprising several detector elements and an anti-scatter grid. The blades 36 of the anti-scatter grid, which are assigned to the detector element 35, are schematically and exemplarily shown in FIG. 2. The dashed lines 37 indicate the angular range, from which radiation could enter the space between the blades 36 and be detected by the detector element 35. FIG. 2 further illustrates several scatter events in the attenuation element 30 and in the object 31.

The beam 42 is scattered in the attenuation element 30 at the scattering location 43, thereby generating a scattered radiation beam 44, which is also scattered in the object 31 at the scattering location 45, thereby generating a further scattered beam 40, which is detected by the detector element 35. The beam 46 is scattered in the attenuation element 30 at the scattering location 47, thereby generating a scattered beam 41, which traverses the object 31 without being scattered again in the object 31 and which is also detected by the detector element 35. The beam 48 traverses the attenuation element 30 without being scattered in the attenuation element 30, but this beam 48 is scattered in the object 31 at the scattering location 49, thereby generating a scattered beam 39, which is also detected by the detector element 35. Finally, the radiation beam 38 traverses the attenuation element 30 and the object 31 without being scattered and this radiation beam, which can be regarded as primary radiation, is also detected by the detector element 35. Thus, the detection value detected by the detector element 35 consists not only of primary radiation 38, but also of scattered radiation 39, 40 and 41. In the following, the double scattered radiation 40 is neglected, because its contribution to the detection values is negligibly small.

It should be noted that the figures are exemplarily and schematically only and are not drawn to scale. For example, in FIG. 2 the detector element 35 is too large in comparison to the overall detector surface 34.

The detection values, which are, in this embodiment, projection values and which have been detected by the detector 6, are provided to a correction device 10 for correcting the detection values with respect to the scattered radiation. In particular, the correction device is adapted to reduce or eliminate the scattered parts 39, 40 and 41 of the detection values, in order to obtain a corrected detection value, which depends preferentially on the primary radiation 38 only. The correction device 10 can be regarded as a correction apparatus.

The correction apparatus 10 comprises an attenuation element scatter values providing unit 12 for providing attenuation element scatter values, which depend on the scattering of the radiation caused by the attenuation element 30. In order to determine these attenuation element scatter values, the radiation source 2, the detector 6 and the collimator 3 are adapted to measure calibration values for different collimations of the radiation 4, wherein the attenuation element scatter values providing unit 12 is adapted to determine the attenuation element scatter values based on the calibration values. The collimator 3 is located between the examination zone 5 and the attenuation element 30, wherein the collimator 3 is adapted to provide collimations, which are different parallel to the z direction or the rotational axis R, i.e. different collimations correspond to different extensions in a direction parallel to the z direction or the rotational axis R. Preferentially, the collimator 3 comprises two blades, which form a slit, wherein different collimations correspond to different slit widths in a direction parallel to the z direction or the rotational axis R.

Figure 3:
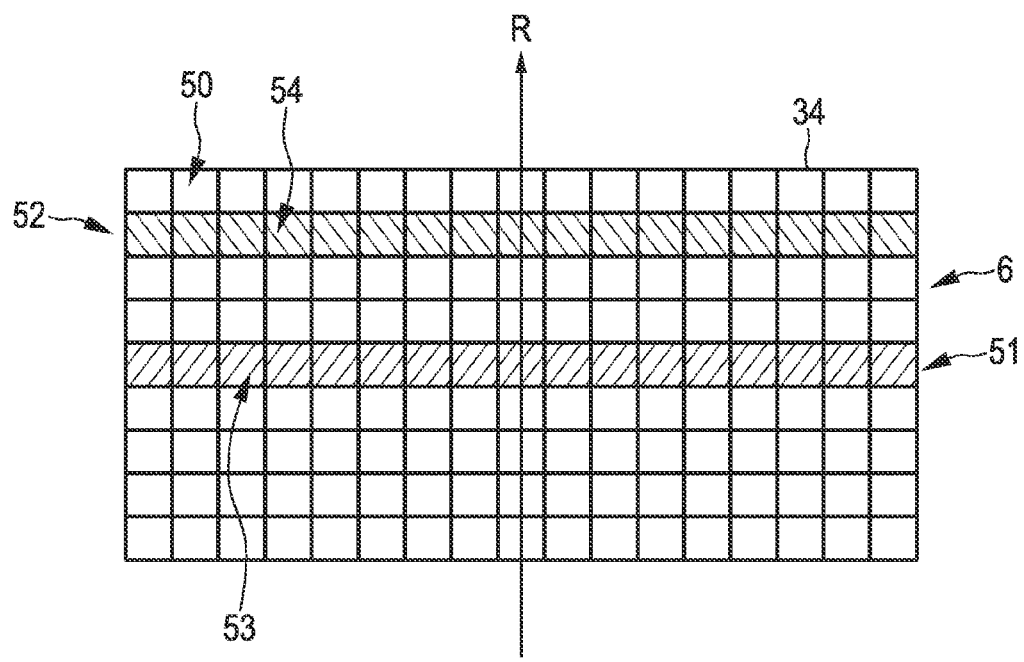
FIG. 3 shows schematically and exemplarily a detection surface of a detector of the imaging apparatus.

Preferentially, the calibration values are determined for the central line 51 of detector elements 50 on the detection surface 34 of the detector 6, while the object 31 is not present. This central line 51 is centered on the detection surface 34 with respect to the rotational axis R and schematically and exemplarily shown in FIG. 3. The central line 51 is perpendicular to the rotational axis R. The collimation by the collimator 3 is modified and detection values of the central line 51 are measured, wherein these detection values measured for different collimations are the calibration values. The different collimations are chosen such that the central line 51 is always completely illuminated by the primary radiation of the radiation 4 emitted by the radiation source 2.

Figure 4:
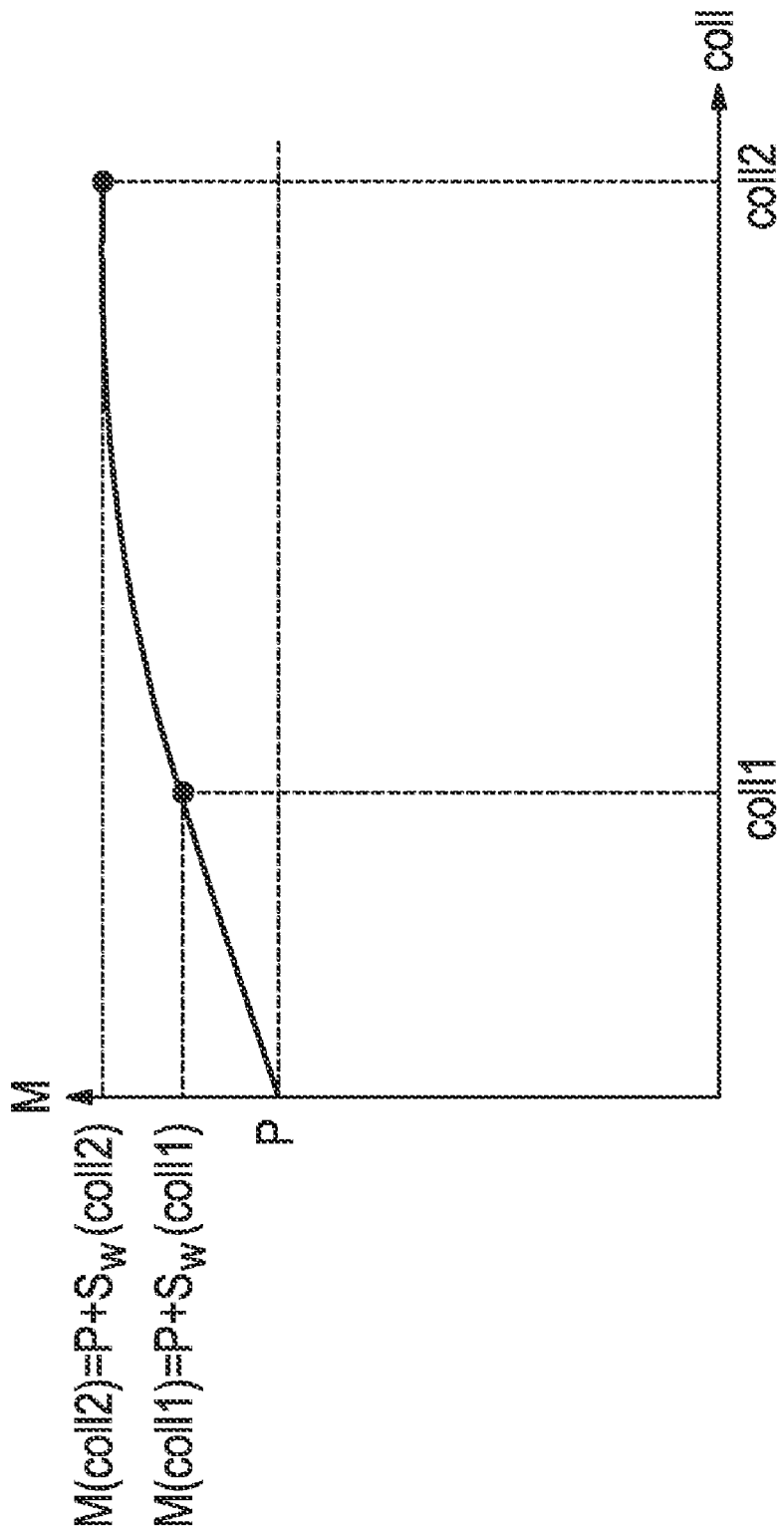
FIG. 4 shows schematically and exemplarily the dependence of calibration values on different collimations.

FIG. 4 shows schematically and exemplarily two calibration values M(coll 1), M(coll 2), which have been measured by a detector element of the central line 51 with two collimations coll 1, coll 2, respectively. The attenuation element scatter values providing unit 12 is adapted to determine the attenuation element scatter values by fitting a function, which considers an attenuation element scatter part and an unscattered part of the calibration values and which depends on the different collimations, to the calibration values. In this embodiment, the function has a square-root dependence for describing the increasing attenuation element scatter part of the calibration values with increasing collimation and a constant dependence for describing the unscattered part of the calibration values, wherein the attenuation element scatter values depend on the attenuation element scatter part. The function, which is fitted to the calibration values, is preferentially defined by following equation:

$$M^{i,j}(\text{coll}) = P^{i,j} + S_w^{i,j}(\text{coll}) \qquad (1)$$

wherein $$S_w^{i,j}(\text{coll}) = b^{i,j}\sqrt{\text{coll}} \qquad (2)$$

In equation (1), $M^{i,j}(\text{coll})$ indicates the detection value, which is, in this case, the calibration value, which has been measured with the collimation coll by the detector element indicated by i and the angular position of the radiation source indicated by j. The term $P^{i,j}$ indicates the unscattered part of the detection value, i.e. of the calibration value in this case, fitted for the detector element indicated by i and the position of the radiation source indicated by j. The attenuation element scatter part of the detection values, i.e. in this case of the calibration value, is indicated by $S^{i,j}(\text{coll})$, which has a square-root behavior as shown in equation (2). The term $b^{i,j}$ indicates a fitting parameter for the square-root behavior of the attenuation element scatter part $S^{i,j}(\text{coll})$.

In this embodiment, the attenuation element scatter value $SPR^{i,j}(\text{coll})$ for the detector element indicated by i and the position of the radiation source indicated j is defined by following equation:

$$SPR^{i,j}(\text{coll}) = \frac{M^{i,j}(\text{coll}) - P^{i,j}}{P^{i,j}} = \frac{M^{i,j}(\text{coll})}{P^{i,j}} - 1 \qquad (3)$$

The attenuation element scatter values $SPR^{i,j}(\text{coll})$ can also be regarded as an attenuation element scatter profile.

In an embodiment, the attenuation element scatter values are not determined depending on the angular position of the radiation source. In this case, calibration values can be determined for a single radiation source position or attenuation element scatter values, which have been determined for different radiation source positions and for the same collimation and the same detector element, can be averaged.

After the attenuation element scatter values have been determined for the central line 51 of the detection surface 34 of the detector 6, an attenuation element scatter value ratio providing unit 13 provides ratios of the attenuation element scatter values of the central line 51, which forms a sub-group of the detector elements 50 on the detection surface 34, to attenuation element scatter values of detector elements outside of the central line 51. In this embodiment, the attenuation element scatter value ratio providing unit 13 is adapted to provide for each combination of a line, which is perpendicular to the rotational axis R and which is not the central line 51, and the central line 51 an attenuation element scatter value ratio, in particular, a single attenuation element scatter value ratio. If, for example, an attenuation element scatter value has been determined for a first detector element 53 of the central line 51, this attenuation element scatter value is multiplied by the ratio, which has been provided for the central line 51 and an outer line 52, in which a second detector element 54 is located, for determining the attenuation element scatter value of the second detector element 54. In this way, for all detector elements outside of the central line 51 attenuation element scatter values are determined by multiplying the respective attenuation element scatter value, which has been determined for a detector element of the central line 51, with the respective ratio provided by the attenuation element scatter value ratio providing unit 13. In another embodiment, the attenuation element scatter value ratio providing unit 13 is adapted to provide for each combination of detector elements, which are located along a line parallel to the rotational axis R, and the respective detector element of the central line 51, which is located on the same line parallel to the rotational axis R, an attenuation element scatter value ratio, i.e. in this further embodiment, not all attenuation element scatter values for the line 52 are determined by multiplying the corresponding attenuation element scatter values determined for the central line 51 with the same attenuation element scatter value ratio.

The attenuation element scatter value ratio providing unit 13 is preferentially a storing unit, in which the attenuation element scatter value ratios are stored, and/or the attenuation element scatter value ratio providing unit 13 can be adapted to determine the attenuation element scatter value ratios by simulating the generation of the attenuation element scatter part of the detection values detected by the detector 6 and, thus, of the attenuation element scatter values by modeling the detection process, i.e. e.g. by modeling the radiation source, the attenuation element and the detector, and by using a Monte-Carlo simulation, wherein the ratios are determined by calculating the respective ratios of the simulated attenuation element scatter values.

In another embodiment, the attenuation element scatter values providing unit can be adapted to determine the attenuation element scatter values by means of Monte Carlo simulations of the entire imaging system, without using the calibration values.

The correction device 10 further comprises an object scatter determination unit 14 for determining object scatter values, which depend on the scattering of the radiation by the object 31. These object scatter values $S_O^{i,j}$ are preferentially determined by a separate method based on convolution with object specific convolution kernels as disclosed in WO 2007/148263 A1, which is herewith incorporated by reference.

The correction device 10 further comprises an air scan values providing unit 15 for providing air scan values and an air scan values correction unit 16 for correcting the air scan values based on the attenuation element scatter values. The determination of the corrected air scan values is preferentially performed in accordance with following equation:

$$P_W^{i,j} = M_W^{i,j} - S_W^{i,j} = M_W^{i,j} \cdot \frac{1}{1 + SPR^{i,j}} \quad (4)$$

wherein $M_w^{i,j}$ indicates the stored air scan value, which has been measured and stored for the detector element indicated by i and the radiation source position indicated by j.

The air scan values providing unit 15 is preferentially a storing unit, in which the air scan values are stored, which have been measured without object and preferentially calculated in advance. It has to be understood, that the air scan values, which have not been corrected, still contain contributions of scattered radiation originating from the attenuation element.

The correction device 10 further comprises a detection values correction unit 17 for correcting the detection values based on the determined attenuation element scatter values. In this embodiment, the detection values correction unit 17 is adapted to correct the detection values based on the determined attenuation element scatter values, the determined object scatter values and the determined corrected air scan values. The detection values correction unit 17 is preferentially adapted to correct detection values $M_O^{i,j}$ according to following equation:

$$M_{O,corr}^{i,j,k} = \frac{M_O^{i,j}}{P_W^{i,j}} - \frac{S_{W,att}^{i,j,k}}{P_W^{i,j}} - \frac{S_O^{i,j,k}}{P_W^{i,j}} \quad (5)$$

wherein $$\frac{S_{W,att}^{i,j,k}}{P_W^{i,j}} = SPR^{i,j} \cdot LP(P_O^{i,j,k}) \quad (6)$$

and $$P_O^{i,j,k} = \begin{cases} \dfrac{M_{Or}^{i,j}}{P_W^{i,j}} & \text{for } k = 1 \\ M_{O,curr}^{i,j,k-1} & \text{for } k > 1 \end{cases} \quad (7)$$

In equation (6), $S_{W,att}^{i,j,k}$ indicates the part of the detection value $M_O^{i,j}$, which has been scattered in the attenuation element 30 and attenuated by the object 31. The term $P_O^{i,j,k}$ indicates the attenuation of the radiation by the object 31 only, and $LP(P_O^{i,j,k})$ indicates low-pass filtered attenuation of the radiation by the object. In this embodiment, $LP(P_O^{i,j,k})$ is regarded as an object attenuation value. In another embodiment, the low-pass filter can be omitted and $P_O^{i,j,k}$ can be regarded as the object attenuation value.

The low-pass filter comprises preferentially low-pass filter coefficients, which are adapted as a function of the system geometry and an acceptance angle of a used anti-scatter grid, which is located between detector elements of the detector. These low-pass filter coefficients are adapted such that the filtered attenuation caused by the object, i.e. the object attenuation value in this case, reflects the average attenuation caused by the object, seen from the detector pixel and integrated over the entire acceptance angle of the anti-scatter grid. Therefore, it is further preferred that the low pass filter is two-dimensional and that the low-pass coefficients are chosen individually for each detector dimension. In one preferred embodiment the low-pass filter is implemented as a binomial low-pass filter.

As an example, coefficients for a suitable low-pass can be found by assuming a virtual radiation source in the center of a detector pixel in the center of the detector and calculating the virtual attenuation due to the anti-scatter grid for a number of discrete positions distributed around the focal spot position whereas the spacing of these positions should have the same effective spacing projected at the iso-center as found between adjacent lines connecting the focal spot and adjacent detector pixels. Coefficients for a suitable two-dimensional binomial low-pass can be found by choosing the coefficients for each separate dimension such that the convolution of both dimensions closely reflects the profile of the above described general low-pass.

It should be noted that, in this embodiment, for correcting the measured detection values the object attenuation value $LP(P_O^{i,j,k})$, i.e. the attenuation by the object only $P_O^{i,j,k}$ is required. However, the term $P_O^{i,j,k}$ used in equation (6) required by equation (5) is equivalent to the term $M_{O,corr}^{i,j,k}$, which is only computed by equation (5) and is therefore not readily available during evaluation of equation (5). Therefore it is a preferred embodiment to use an iterative procedure where for the first iteration with the iteration index $k=1$ $P_O^{i,j,k}$ is initialized with the measured detection value divided by the corrected air scan value and in each further iteration $P_O^{i,j,k}$ is updated by the corrected value $M_{O,corr}^{i,j,k}$ of the last iteration. The iteration can be terminated when it is observed that from one iteration to the next the change of $M_{O,corr}^{i,j,k}$ is smaller than a predefined threshold. In another embodiment the number of iterations is fixed to a predefined number, e.g. 3.

In equations (4) to (6), it is assumed that the variables correspond to the same collimation. The dependence on the collimation is therefore not shown in these equations.

The correction device 10 further comprises a reconstruction unit 18 for reconstructing an image of the region of interest from the corrected detection values $M_{O,corr}^{i,j}$. The reconstruction unit 18 is preferentially adapted to perform a backprojection algorithm for reconstructing an image of the region of interest. In another embodiment, the reconstruction unit 18 can be adapted to use another reconstruction algorithm, for example, a radon inversion.

The image reconstructed by the reconstruction unit 18 is provided to a display unit 11 for displaying the reconstructed image.

Also the correction device is preferably controlled by the control unit 9.

Figure 5:
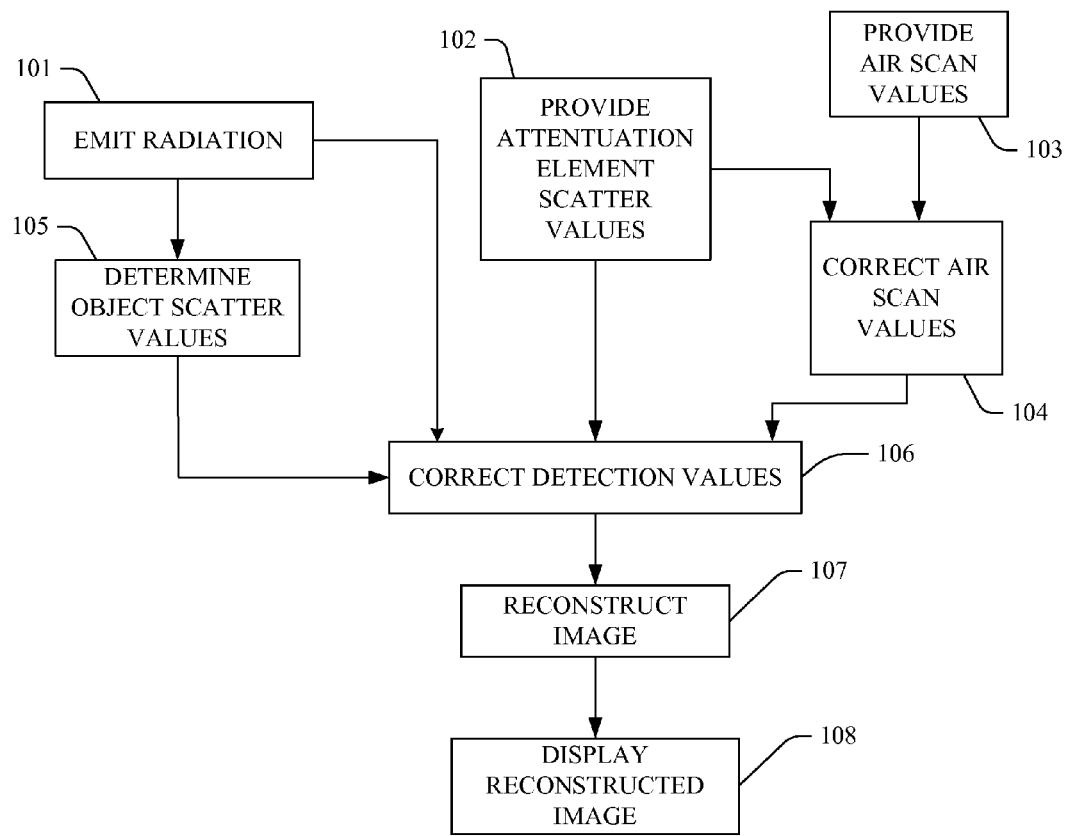
FIG. 5 shows a flow chart illustrating an embodiment of an imaging method for generating an image of a region of interest of an object.

In the following an imaging method for generating an image of a region of interest of an object will be described with reference to a flow chart shown in FIG. 5.

The imaging method for generating an image of a region of interest of an object is, in this embodiment, a computed tomography imaging method. In step 101, the radiation source 2 rotates around the rotational axis R and the object or the examination zone 5 is not moved, i.e. the radiation source 2 travels along a circular trajectory around the object or the examination zone 5. In another embodiment, the radiation source 2 can move along another trajectory, for example, a helical trajectory, relative to the object. The radiation source 2 emits radiation traversing the attenuation element and the object at least in the region of interest. The radiation, which has traversed the attenuation element and the object, is detected by the detector 6, which generates measured detection values being projection values. The measured detection values are transferred to the correction device 10.

In step 102, attenuation element scatter values are provided, which depend on the scattering of the radiation 4 caused by the attenuation element 30, and in step 103 the air scan values providing unit 15 provides air scan values. Steps 101, 102 and 103 can be performed independently from each other. In step 104, the air scan value correction unit 16 corrects the air scan values based on the attenuation element scatter values. This step 104 can be performed before or after step 101 is performed. Preferentially, step 104 is performed before step 101.

In step 105, the object scatter determination unit 14 determines object scatter values depending on the measured detection values detected in step 101, and in step 106 the detection values correction unit 17 corrects the detection values based on the determined object scatter values, the provided attenuation element scatter values and the corrected air scan values.

The corrected detection values are used for reconstructing an image of the region of interest by the reconstruction unit 18 in step 107, and in step 108 the reconstructed image is shown on the display unit 11.

Figure 6:
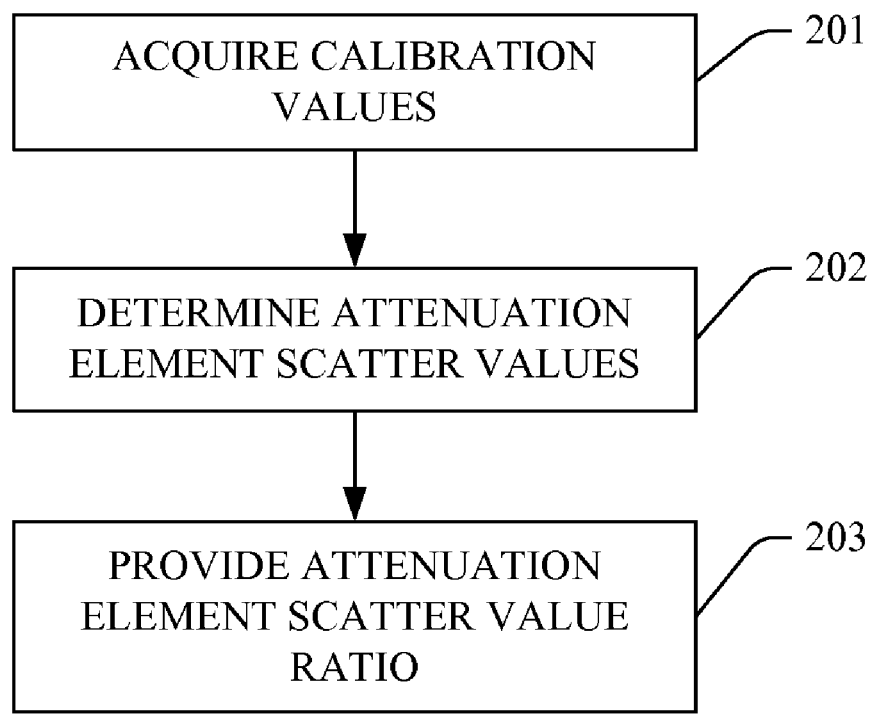
FIG. 6 shows a flow chart illustrating a determination of attenuation element scatter values.

In the following an embodiment of a determination of attenuation element scatter values will be described with reference to a flow chart shown in FIG. 6.

In step 201, the detection surface 34 of the detector 6 is illuminated by radiation having different collimations, wherein for each collimation the detection values of the central line 51 are read out. These detection values are regarded as calibration values. For each measurement of calibration values, the central line 51 is completely illuminated by the collimated radiation.

In step 202, the attenuation element scatter values providing unit 12 determines attenuation element scatter values, which depend on the scattering of the radiation 4 caused by the attenuation element 30, based on the calibration values. In this embodiment, the above described fit function having the square-root behavior is fitted to the calibration values and equation (3) is used for determining the attenuation element scatter values for the central line 51.

In step 203, the attenuation element scatter value ratio providing unit 13 provides attenuation elements scatter value ratios of the attenuation element scatter values of the central line 51 to attenuation element scatter values of detector elements in other lines on the detection surface 34. Furthermore, these attenuation element scatter value ratios are multiplied with the attenuation element scatter value determined for the central line 51 for determining attenuation element scatter value also for the other lines of the detection surface 34.

If in an embodiment the calibration values are used also as air scan values or vice versa, step 201 or step 103, respectively, can be omitted.

The correction device 10 can also be regarded as a stand-alone system, which is provided with measured detection values, which are, for example, acquired in step 101, wherein the correction device comprises at least the attenuation element scatter values providing unit for providing attenuation element scatter values, which depend on scattering of the radiation caused by the attenuation element, and a detection values correction unit for correcting the detection values based on the provided attenuation element scatter values. This correction device, which can also be regarded as a correction apparatus, preferentially further comprises the reconstruction unit for reconstructing an image of the region of interest from the corrected detection values. A corresponding correction method comprises at least the step of providing the detection values, of providing the attenuation element scatter values and of correcting the detection values based on the provided attenuation element scatter values.

While acquiring the calibration values in step 201, several acquisitions can be performed, in particular, several acquisitions at different positions of the radiation source can be performed, in order to generate redundant calibration values, which are preferentially averaged, in particular, in order to keep quantum noise small.

During the determination of the attenuation element scatter values in step 202, in particular, by using the fit function having a square-root behavior, preferentially only calibration values are used, which have been detected for a larger collimation, i.e. which have been detected for a larger blade opening, in particular, only calibration values are used, which correspond to collimations larger than a predefined collimation value. This predefined collimation value is preferentially chosen such that the quality of the calibration values is large enough for being used to determine reliable attenuation element scatter values. In particular, preferentially only calibration values are used, which have been measured with a collimation, which corresponds to eight or more lines of detector elements on the detection surface 34 perpendicular to the rotational axis R.

Figure 7:
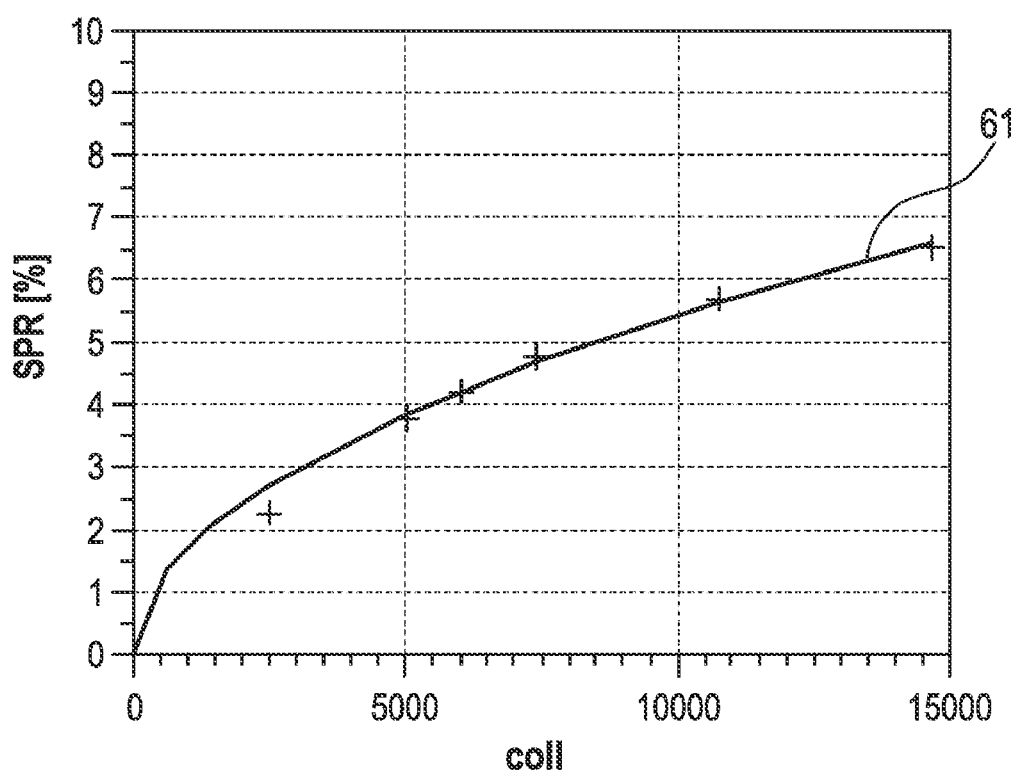
FIG. 7 shows schematically and exemplarily a dependence of attenuation element scatter values on different collimations and FIG. 8 shows schematically and exemplarily attenuation element scatter values depending on different collimations and different detector elements, which are located along a central line on a detection surface of the detector.

FIG. 7 shows schematically and exemplary attenuation element scatter values SPR, which have been determined for a detector element and a fixed radiation source position and for different collimations coll. In this embodiment, the collimation is defined by the width of a slit of the collimator 3 in the direction of the rotational axis R. The crosses indicate measured calibration values and the lines indicate the fitted square-root part of the fit function.

Figure 8:
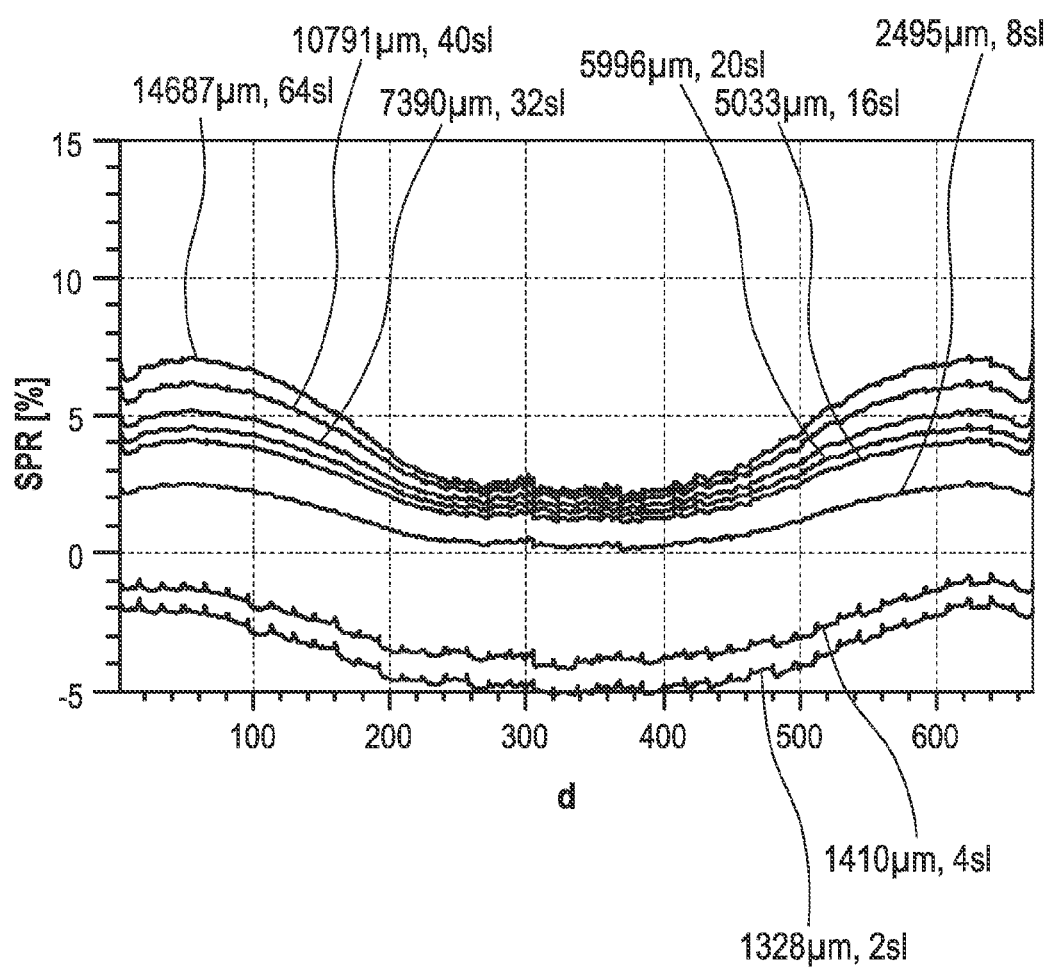

FIG. 8 shows schematically and exemplary attenuation element scatter values SPR, which have been determined for a central line of a detection surface of a detector depending on the different detector elements d in the central line and depending on different collimations, wherein the different collimations are defined by the width of a slit of the collimator 3 in a direction parallel to the rotational axis. The term "x sl", i.e., for example, "4 sl", indicates that the collimation is chosen such that only x lines perpendicular to the rotational axis R are illuminated.

The above described method allows to estimate the attenuation element scatter effect detected in presence of an object like a patient by propagating the attenuation element scatter through the attenuation seen in each view. The determined attenuation element scatter values are therefore multiplied by the attenuation according to the attenuation of the primary radiation, i.e. the radiation, which has not been scattered, of the current projection, i.e. of the current radiation source position. In order to account for a wider range of incident angles of scattered radiation as compared to primary radiation originating only from the focus of the radiation source and, therefore, in order to account for the different paths of the attenuation, the attenuation is preferentially computed by averaging over a local region of a primary attenuation profile by means of a low-pass filter. Thereby, the degree of required low-pass filter is specified based on the angular transmission function of the anti-scatter grid.

The detection values correction unit can further be adapted to perform a beam hardening correction on the detection values, in order to further improve the quality of the detection values. If the imaging apparatus is a computed tomography apparatus, the scatter correction and the beam hardening correction can be combined in order to provide an improved computed tomography image chain that deals with scatter in a physically appropriate way and fully separates scatter effects from the other corrections in an imaging chain.

Although in the above described embodiments, the imaging apparatus is preferentially a computed tomography scanner, in other embodiments, the imaging apparatus can be another imaging modality, for example, another X-ray imaging apparatus or an imaging apparatus using another kind of radiation like a nuclear imaging apparatus such as a positron emission tomography apparatus or a single photon emission computed tomography apparatus. In particular, the imaging apparatus can be a flat detector cone-beam computed tomography apparatus based on e.g. C-arms, on-board imagers in radiation therapy, or hybrid cone-beam computed tomography apparatuses in nuclear medicine.

The object, which is imaged in the imaging apparatus, is preferentially a patient. However, it can also be another object like a technical object, for example, baggage, which has to be inspected at an airport.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Calculations and determinations, like the calculation and determination of the attenuation element scatter values and the reconstruction of the image, performed by one or several units or devices can be performed by any other number of units or devices. For example, the calculations for the determination of the attenuation element scatter values, for the correction of the air scan values and for reconstructing the image can be performed by a single unit or by any other number of different units. The calculations and determinations and/or the control of the imaging apparatus and/or of the correction apparatus in accordance with the above described imaging method and/or correction method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An imaging apparatus for generating an image of a region of interest of an object, the imaging apparatus comprising:
    a radiation source for emitting radiation;
    a detector for measuring the radiation after having traversed the region of interest and for generating measured detection values depending on the measured radiation;
    an examination zone, in which the object is to be located;
    an attenuation element for attenuating the radiation before traversing the region of interest;
    a collimator for collimating the radiation emitted by the radiation source, the collimator being located between the attenuation element and the examination zone, wherein the radiation source, the detector and the collimator measure calibration values for different collimations of the radiation and wherein the attenuation element scatter values providing unit determines the attenuation element scatter values based on the calibration values, wherein the attenuation element scatter values providing unit determines the attenuation element scatter values by fitting a function, which considers an attenuation element scatter part and an unscattered part of the calibration values and which depends on the different collimations, to the calibration values;

an attenuation element scatter values providing unit for providing attenuation element scatter values, which depend on scattering of the radiation caused by the attenuation element;

a detection values correction unit for correcting the measured detection values based on the provided attenuation element scatter values; and a reconstruction unit for reconstructing an image of the region of interest from the corrected detection values.

2. The imaging apparatus as claimed in claim 1, wherein the function has a square-root dependence for describing the increasing attenuation element scatter part of the calibration values with increasing collimation and a constant dependence for describing the unscattered part of the calibration values, wherein the attenuation element scatter value depends on the attenuation element scatter part.

3. The imaging apparatus as claimed in claim 1, wherein the imaging apparatus further comprises:
an air scan values providing unit for providing air scan values;
an air scan values correction unit for correcting the air scan values based on the attenuation element scatter values,
wherein the detection values correction unit is adapted to correct the measured detection values based on the corrected air scan values.

4. The imaging apparatus as claimed in claim 1, wherein the detection values correction unit is adapted to adapt the attenuation element scatter values to the attenuation of radiation, which has been scattered in the attenuation element and attenuated by the object if the object is present between the attenuation element and the detector, and to correct the measured detection values based on the adapted attenuation element scatter values.

5. The imaging apparatus as claimed in claim 4, wherein the adaptation of the attenuation element scatter values is performed by multiplying the respective attenuation element scatter value by a respective object attenuation value that depends on the attenuation caused by the object.

6. The imaging apparatus as claimed in claim 1, wherein the imaging apparatus comprises:
an air scan values providing unit for providing air scan values
an air scan values correction unit for correcting the air scan values based on the attenuation element scatter values;
the detection values correction unit is adapted to correct the measured detection values iteratively, wherein
in an iteration step the corrected detection value is calculated by subtracting the respective attenuation element scatter value multiplied by a respective object attenuation value, that depends on the attenuation caused by the object, from the respective measured detection value divided by the respective corrected air scan value,
initially the respective object attenuation value depends on the respective measured detection value divided by the respective corrected air scan value, and in further iteration steps the object attenuation value depends on a calculated respective corrected detection value.

7. A correction apparatus for correcting measured detection values, the correction apparatus being provided with the detection values generated depending on measured radiation, which has been emitted by a radiation source and which has traversed an attenuation element for attenuating the radiation before traversing a region of interest, the correction apparatus comprising:
an attenuation element scatter values providing unit that determines the attenuation element scatter values by fitting a function, which considers an attenuation element scatter part and an unscattered part of calibration values for different measured collimations, and which depends on the different collimations, to the calibration values,
a detection values correction unit for correcting the measured detection values based on the provided attenuation element scatter values.

8. An imaging method for imaging a region of interest of an object, the imaging method comprising:
emitting radiation by a radiation source;
attenuating the radiation before traversing the region of interest by an attenuation element;
collimating the emitted radiation emitted by the radiation source
measuring calibration values for different collimations of the emitted radiation;
determining attenuation element scatter values by fitting a function, which considers an attenuation element scatter part and an unscattered part of the calibration values and which depends on the different collimations, to the calibration values;
measuring the radiation after having traversed the region of interest and generating measured detection values depending on the measured radiation by a detector;
providing attenuation element scatter values, which depend on the scattering of the radiation caused by the attenuation element, by an attenuation element scatter values providing unit;
correcting the measured detection values based on the provided attenuation element scatter values by a detection values correction unit; and
reconstructing an image of the region of interest from the corrected detection values by a reconstruction unit.

9. A non-transitory computer readable medium having an imaging computer program for imaging a region of interest of an object stored thereon, the imaging computer program comprising program code means for causing an imaging apparatus as defined in claim 1 to carry out the steps of:
emitting radiation by a radiation source;
attenuating the radiation before traversing the region of interest by an attenuation element;
measuring the radiation after having traversed the region of interest and generating measured detection values depending on the measured radiation by a detector;
providing attenuation element scatter values, which depend on the scattering of the radiation caused by the attenuation element, by an attenuation element scatter values providing unit;
correcting the measured detection values based on the provided attenuation element scatter values by a detection values correction unit; and
reconstructing an image of the region of interest from the corrected detection values by a reconstruction unit, when the imaging computer program is executed on a processor.

10. A non-transitory computer readable medium having a correction computer program for correcting measured detection values stored thereon, the correction computer program comprising program code means for causing a correction apparatus as defined in claim 7 to carry out the steps of:

providing the measured detection values generated depending on measured radiation, which has been emitted by a radiation source and which has traversed an attenuation element for attenuating the radiation before traversing a region of interest;

providing attenuation element scatter values, which depend on scattering of the radiation caused by the attenuation element by an attenuation element scatter values providing unit; and correcting the measured detection values based on the provided attenuation element scatter values by a detection values correction unit, when the correction computer program is executed on a processor.

11. The imaging apparatus as claimed in claim 10, wherein the detector comprises a two-dimensional detector surface, wherein the sub-group of detector elements is a line of detector elements on the detector surface.

12. The imaging apparatus as claimed in claim 10, wherein the imaging apparatus further comprises:
an air scan values providing unit for providing air scan values and
an air scan values correction unit for correcting the air scan values based on the attenuation element scatter values, wherein the detection values correction unit corrects the measured detection values based on the corrected air scan values.

13. The imaging apparatus as claimed in claim 10, wherein the detection values correction unit adapts the attenuation element scatter values to the attenuation of radiation, which has been scattered in the attenuation element and attenuated by the object if the object is present between the attenuation element and the detector, and to correct the measured detection values based on the adapted attenuation element scatter values.

14. The imaging apparatus as claimed in claim 13, wherein the adaptation of the attenuation element scatter values is performed by multiplying the respective attenuation element scatter value by a respective object attenuation value that depends on the attenuation caused by the object.

15. The imaging apparatus as claimed in claim 10, wherein the imaging apparatus comprises:
an air scan values providing unit for providing air scan values;
an air scan values correction unit for correcting the air scan values based on the attenuation element scatter values, wherein the detection values correction unit corrects the measured detection values iteratively, wherein in an iteration step the corrected detection value is calculated by subtracting the respective attenuation element scatter value multiplied by a respective object attenuation value, that depends on the attenuation caused by the object, from the respective measured detection value divided by the respective corrected air scan value, initially the respective object attenuation value depends on the respective measured detection value divided by the respective corrected air scan value, and in further iteration steps the object attenuation value depends on a calculated respective corrected detection value.

16. An imaging apparatus for generating an image of a region of interest of an object, the imaging apparatus comprising:
a radiation source for emitting radiation;
a detector for measuring the radiation after having traversed the region of interest and for generating measured detection values depending on the measured radiation;
an examination zone, in which the object is to be located;
an attenuation element for attenuating the radiation before traversing the region of interest;
a collimator for collimating the radiation emitted by the radiation source, the collimator being located between the attenuation element and the examination zone, wherein the radiation source, the detector and the collimator measure calibration values for different collimations of the radiation and wherein the attenuation element scatter values providing unit determines the attenuation element scatter values based on the calibration values, wherein
the detector comprises several detector elements;
the radiation source, the detector and the collimator measures calibration values for different collimations of the radiation for a sub-group of the detector elements;
the attenuation element scatter values providing unit determines the attenuation element scatter values for the sub-group of the detector elements;
the imaging apparatus further comprises an attenuation element scatter value ratio providing unit that provides ratios of the attenuation element scatter values of the sub-group of detector elements to attenuation element scatter values of detector elements outside of the sub-group; and
the attenuation element scatter values providing unit determines attenuation element scatter values for detector elements outside of the sub-group by multiplying the attenuation element scatter values for the sub-group by the provided ratios.

* * * * *